United States Patent
Song et al.

(10) Patent No.: US 9,766,247 B2
(45) Date of Patent: Sep. 19, 2017

(54) RAPID METHOD TO ANALYZE UBIQUITIN-PROTEASOME ACTIVITY AND TO SCREEN FOR UBIQUITIN-PROTEASOME INHIBITOR

(71) Applicant: KOREA INSTITUTE OF SCIENCE AND TECHNOLOGY, Seoul (KR)

(72) Inventors: Eun Joo Song, Seoul (KR); Hyunjung Lee, Seoul (KR); Eunmi Ban, Seoul (KR); Eunice EunKyeong Kim, Seoul (KR); Young Sook Yoo, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 118 days.

(21) Appl. No.: 14/513,774

(22) Filed: Oct. 14, 2014

(65) Prior Publication Data
US 2015/0362480 A1    Dec. 17, 2015

(30) Foreign Application Priority Data
Jun. 13, 2014    (KR) .......................... 10-2014-0072350

(51) Int. Cl.
*G01N 33/50*    (2006.01)
*G01N 33/58*    (2006.01)
*G01N 33/68*    (2006.01)

(52) U.S. Cl.
CPC .......... *G01N 33/68* (2013.01); *G01N 33/502* (2013.01); *G01N 2500/02* (2013.01)

(58) Field of Classification Search
CPC ... G01N 2500/02; G01N 33/502; G01N 33/68
USPC ....................................................... 435/23
IPC ............................................ G01N 33/50,33/58
See application file for complete search history.

(56) References Cited

U.S. PATENT DOCUMENTS

2013/0052660 A1*  2/2013  Lee ................... G01N 21/6428
                                                                  435/7.8

FOREIGN PATENT DOCUMENTS

JP    P2007-282628 A    11/2007
KR    10-2013-0023057 A    3/2013

OTHER PUBLICATIONS

Peters et al., 1994. Distinct 19 S and 20 S Subcomplexes of the 26 S Proteasome and Their Distribution in the Nucleus and the Cytoplasm. The Journal of Biological Chemistry, vol. 269, pp. 7709-7718.*
Nandi et al., 2006. The ubiquitin-proteasome system. Journal of Bioscience, vol. 31, pp. 137-155.*
Rajkumar et al., 2005. Proteasome inhibition as a novel therapeutic target in human cancer; Journal of Clinical Oncology, vol. 23, pp. 630-639.*
Swearingen et al., "Quantification of green fluorescent protein in cellular supernatant by capillary electrophoresis with laser-induced fluorescence detection for measurement of cell death", *Talanta*, 2010, pp. 948-953, vol. 81.
Myeku et al., "Dynamics of the Degradation of Ubiquitinated Proteins by Proteasomes and Autophagy: Association With Sequestosome 1/p62", *Journal of Biological Chemistry*, Jun. 24, 2011, pp. 22426-22440, vol. 286, No. 25.
Lee et al., "Rapid monitoring of proteasome activity in cells by transfection of reporter genes using capillary electrophoresis", Thesis F-5 of *2014 KSBMB Annual Meeting*, May 14-16, 2014, 2 pp.

* cited by examiner

*Primary Examiner* — Debbie K Ware
*Assistant Examiner* — Kailash C Srivastava
(74) *Attorney, Agent, or Firm* — Goldilocks ZONE IP LAW

(57) ABSTRACT

Provided are a method of analyzing ubiquitin-proteasome activity with respect to a target polypeptide and a method of screening a ubiquitin-proteasome inhibitor. According to the provided methods, the pattern of lysis of a target polypeptide by a ubiquitin-proteasome in target cells may be quantitatively analyzed in a rapid and highly sensitive way, a ubiquitin-proteasome inhibitor may be screened in a rapid and highly sensitive way, and an anticancer agent and the activity thereof may be rapidly screened.

14 Claims, 8 Drawing Sheets

RAPID METHOD TO ANALYZE UBIQUITIN-PROTEASOME ACTIVITY AND TO SCREEN FOR UBIQUITIN-PROTEASOME INHIBITOR

RELATED APPLICATION

This application claims the benefit of Korean Patent Application No. 10-2014-0072350, filed on Jun. 13, 2014, in the Korean Intellectual Property Office, the disclosure of which is incorporated herein in its entirety by reference.

BACKGROUND

1. Field

One or more embodiments of the present invention relate to a method of analyzing ubiquitin-proteasome activity and a method of screening a ubiquitin-proteasome inhibitor by using the same.

2. Description of the Related Art

A ubiquitin proteasome system is an important regulatory mechanism in cell growth and division, cell cycle, intracellular signal transduction, and cell apoptosis. Through the regulatory mechanism, a protein acting as a substrate is degraded by a proteasome. In the proteolytic process by the ubiquitin proteasome system, multiple ubiquitin protein chains form a covalent bond with a substrate, and the resulting product is recognized and degraded by a 26S proteasome consisting of a 20S complex and 19S particles. In this process, ubiquitin proteins are bound to a substrate by a ubiquitin-activating enzyme E1, a ubiquitin-conjugating enzyme E2, and a ubiquitin ligase E3, and the resulting ubiquitinated proteins are degraded by a proteasome. Since it is known that the ubiquitin-proteasome system affects the onset of various cancers, neurodegenerative diseases, metabolic disorders, viral diseases, cardiac diseases, and aging-related diseases and the inhibition of proteasome activity suppresses apoptosis and proliferation of cancer cells, there is an increasing interest in the development of a proteasome inhibitor as an anticancer agent.

Recently, as methods of quantitatively observing substrates of the ubiquitin-proteasome system, fluorescent microscopy, flow cytometry, high-throughput screening, pulse chase labelling method, and immunoblotting are used. However, since these methods include many experimental steps, these methods are complicated, time-consuming, and low in quantitative accuracy.

Therefore, there is a need for developing a method of quantitatively analyzing ubiquitin-proteasome activity in a short period of time and a method of screening a proteasome inhibitor.

SUMMARY

One or more embodiments of the present invention provide a method of quantitatively analyzing ubiquitin-proteasome activity with respect to a target polypeptide.

One or more embodiments of the present invention provide a method of screening a ubiquitin-proteasome inhibitor.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
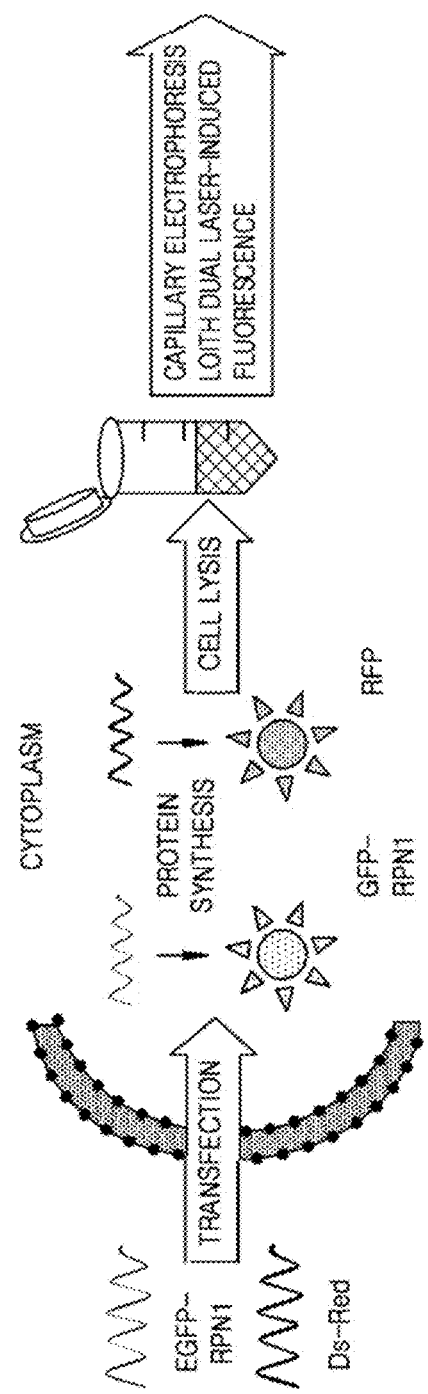
FIG. 1 is a schematic diagram of a method of quantitatively analyzing a ubiquitin-proteasome-dependent substrate according to one aspect of the present invention. A polynucleotide encoding a fusion protein including a green fluorescent protein (GFP) and a ubiquitin-proteasome-dependent substrate ribophorin I (RPN1), and a ubiquitin-proteasome-independent substrate Ds-Red are cotransduced to cells, and then the cells are lysed; The GFP-RPN1 fusion protein expressed in the cells or a red fluorescent protein (RFP) is verified by capillary electrophoresis with dual laser-induced fluorescence (CE-dual LIF)

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

One aspect of the present invention provides a method of quantitatively analyzing ubiquitin-proteasome activity with respect to a target polypeptide, the method including simultaneously or sequentially adding a first polynucleotide encoding a fusion protein including a target polypeptide and a first fluorescent protein, and a second polynucleotide encoding a second fluorescent protein to a culture solution including cells to simultaneously or sequentially introduce the first polynucleotide and the second polynucleotide to the cells;

obtaining cells from the culture solution and lysing the obtained cells to obtain cell lysis solution;

separating the obtained cell lysis solution by capillary electrophoresis and simultaneously or sequentially quantifying the fluorescence intensity of the fusion protein including the target polypeptide and the first fluorescent protein, and the second fluorescent protein; and analyzing the fluorescence intensity of the fusion protein including the target polypeptide and the first fluorescent protein relative to the fluorescence intensity of the second fluorescent protein to quantify intracellular degradation of the target polypeptide by a ubiquitin-proteasome.

The method includes simultaneously or sequentially adding a first polynucleotide encoding a fusion protein including a target polypeptide and a first fluorescent protein, and a second polynucleotide encoding a second fluorescent protein to a culture solution including cells to simultaneously or sequentially introduce the first polynucleotide and the second polynucleotide to the cells.

The target polypeptide means a polypeptide which is used to verify whether a ubiquitin may be degraded by a ubiquitin-proteasome.

The first fluorescent protein or the second fluorescent protein may not be degraded by a ubiquitin-proteasome. The first fluorescent protein or the second fluorescent protein may be degraded independently on a ubiquitin. The first fluorescent protein and the second fluorescent protein may emit light of different wavelengths. For example, the first fluorescent protein may be a green fluorescent protein, and the second fluorescent protein may be a red fluorescent protein, but the first fluorescent protein and the second fluorescent protein are not limited thereto. The green fluorescent protein may be, for example, EGFP (Clontech). The red fluorescent protein may be, for example, Ds-Red (Clontech), mCherry, tdTomato, mStrawberry, or J-Red (Evrogen).

The fusion protein may be a protein including a first fluorescent protein and a target polypeptide. The fusion protein may be a first fluorescent protein and a target polypeptide from an N-terminal thereof.

The polynucleotide may include a vector which may be expressed in a cell. The vector may be a plasmid vector or a viral vector, but is not limited thereto. The vector may include a transcription regulatory region in which a protein is expressed in a cell. The transcription regulatory region may include a promoter.

The cell may be a cell of a mammal. The mammal may be, for example, a human, dog, cow, horse, rabbit, rat, or mouse. The cell may be a normal cell or a cell including a mutated ubiquitin or a mutated proteasome. The cell may be, for example, a cancer cell, a neuron, a cardiac myocyte, or an immunocyte.

A polynucleotide may be introduced to a cell by a method known in this art. For example, a polynucleotide may be introduced to a cell by adding a polynucleotide which is mixed with lipofectamine to a cell culture solution.

The method may include obtaining cells from the culture solution and lysing the obtained cells to obtain cell lysis solution. Cells may be obtained and lysed by methods known in this art. Cells may be lysed by a chemical method or a physical method. A chemical method may be, for example, use of a cell lysis solution including a surfactant. A physical method may be, for example, sonication or repeated freezing and thawing.

The method may include separating the obtained cell lysis solution by capillary electrophoresis and simultaneously or sequentially quantifying the fluorescence intensity of the fusion protein including the target polypeptide and the first fluorescent protein, and the fluorescence intensity of the second fluorescent protein.

Capillary electrophoresis is performed by dipping a tip of a capillary in an electrolyte solution and applying direct current with high voltage to separate samples included in the capillary through electrophoresis. The inner diameter of the capillary may be, for example, from about 40 µm to about 100 µm, from about 45 µm to about 90 µm, from about 50 µm to about 80 µm, or from about 50 µm to about 75 µm. The length of the capillary may be for example, from about 10 cm to 70 cm, from about 20 cm to 76 cm, or from about 30 cm to 50 cm. Capillary electrophoresis may be performed in the presence of sodium dodecylsulfate (SDS) at a concentration from about 3 mM to about 20 mM, from about 5 mM to about 15 mM, or from about 7 mM to about 10 mM. Capillary electrophoresis may be performed in the presence of a running buffer solution from about pH 4 to about pH 11, from about pH 6 to about pH 11, from about pH 8 to about pH 11, or from about pH 9 to about pH 10.

Quantifying of the fluorescence intensity may be performed by using a dual fluorescence detector. A dual fluorescence detector is an instrument for simultaneously or sequentially detecting fluorescence at two or more wavelengths.

The method includes analyzing the fluorescence intensity of the fusion protein including the target polypeptide and the first fluorescent protein relative to the fluorescence intensity of the second fluorescent protein to quantify the degradation of the target polypeptide by a ubiquitin-proteasome.

The fluorescence intensity of the second fluorescent protein may be measured to correct the difference of the efficiency of introducing a polynucleotide to cells.

The method may be used to verify whether a target polypeptide is degraded by a ubiquitin-proteasome and to quantitatively analyze the degraded amount. Therefore, the ubiquitin-proteasome activity with respect to a target polypeptide may be quantitatively analyzed.

The method may be performed in vitro.

The method may further include analyzing the variation of the intracellular degradation of a target polypeptide to quantitatively analyze the variation of ubiquitin-proteasome activity with respect to a target polypeptide.

Another aspect to the present invention provides a method of screening a ubiquitin-proteasome inhibitor, the method including simultaneously or sequentially adding a first polynucleotide encoding a fusion protein including a polypeptide, which is degraded by a ubiquitin-proteasome, and a first fluorescent protein, and a second polynucleotide encoding a second fluorescent protein to a culture solution including cells to simultaneously or sequentially introduce the first polynucleotide and the second polynucleotide to cells;
  adding a ubiquitin-proteasome inhibitor candidate substance to the culture solution;
  obtaining cells from the culture solution and lysing the obtained cells to obtain cell lysis solution;
  separating the obtained cell lysis solution by capillary electrophoresis and simultaneously or sequentially quantifying the fluorescence intensity of the fusion protein including the polypeptide and the first fluorescent protein, and the fluorescence intensity of the second fluorescent protein; and
  comparing the fluorescence intensity of the fusion protein including the polypeptide and the first fluorescent protein relative to the fluorescence intensity of the second fluorescent protein with the fluorescence intensity of a negative control group to which a ubiquitin-proteasome inhibitor candidate substance is not added to screen a ubiquitin-proteasome inhibitor.

The first fluorescent protein, the second fluorescent protein, cells, introducing, obtaining, lysis, capillary electrophoresis, and fluorescence intensity are described above.

The method includes simultaneously or sequentially adding a first polynucleotide encoding a fusion protein including a polypeptide, which is degraded by a ubiquitin-proteasome, and a first fluorescent protein, and a second polynucleotide encoding a second fluorescent protein to a culture solution including cells to simultaneously or sequentially introduce the first polynucleotide and the second polynucleotide to cells.

The polypeptide is degraded by a ubiquitin-proteasome and may be a polypeptide known in this art. For example, the polypeptide may be RPN1.

The method includes adding a ubiquitin-proteasome inhibitor candidate to the culture solution. A ubiquitin-proteasome inhibitor candidate substance may be a substance which may be predicted to function as a ubiquitin-proteasome inhibitor.

The method includes obtaining cells from the culture solution and lysing the obtained cells to obtain cell lysis solution.

The method includes separating the obtained cell lysis solution by capillary electrophoresis and simultaneously or sequentially quantifying the fluorescence intensity of the fusion protein including the polypeptide and the first fluorescent protein, and the fluorescence intensity of the second fluorescent protein.

The method includes comparing the fluorescence intensity of the fusion protein including the polypeptide and the first fluorescent protein relative to the fluorescence intensity of the second fluorescent protein with the fluorescence intensity of a negative control group to which a ubiquitin-proteasome inhibitor candidate substance is not added to screen a ubiquitin-proteasome inhibitor. The measured fluorescent intensity of the fusion protein is compared with the fluorescent intensity of the negative control group. When the measured fluorescent intensity of the fusion protein is higher than the fluorescent intensity of the negative control group, the ubiquitin-proteasome inhibitor candidate substance may be screened as a ubiquitin-proteasome inhibitor.

The ubiquitin-proteasome inhibitor may be a candidate substance for treating a cancer, a degenerative brain disease, a cardiovascular disease, an autoimmune disease, or a combination thereof.

The method may further include analyzing the variation of the intracellular degradation of a target polypeptide to quantitatively analyze the variation of ubiquitin-proteasome activity with respect to a ubiquitin-proteasome inhibitor candidate substance. For example, the variation of ubiquitin-proteasome activity may be quantitatively analyzed according to the kind or amount of a ubiquitin-proteasome inhibitor candidate substance.

FIG. 1 is a schematic diagram showing a quantitative method of analyzing a ubiquitin-proteasome-dependent substrate according to one aspect of the present invention. A polynucleotide encoding a fusion protein including a green fluorescent protein (GFP) and a ubiquitin-proteasome-dependent substrate ribophorin I (RPN1), and a ubiquitin-proteasome-independent substrate Ds-Red are cotransduced to cells, and then the cells are lysed. The GFP-RPN1 fusion protein expressed in the cells or a red fluorescent protein (RFP) is verified by capillary electrophoresis with dual laser-induced fluorescence (CE-dual LIF).

Hereinafter, the present invention will be described in further detail with reference to examples. It will be obvious to a person having ordinary skill in the art that these examples are illustrative purposes only and are not to be construed to limit the scope of the present invention.

EXAMPLE 1

Verification of Ubiquitin-Proteasome-Dependent Protein and Ubiquitin-Proteasome-Independent Protein 1.1 Preparation of Vectors for Expressing Ubiquitin-Proteasome-Dependent Protein or Ubiquitin-Proteasome-Independent Protein To monitor a ubiquitin-proteasome-dependent protein RPN1 (ribophorin I), a plasmid vector enabling to express a fusion protein including a green fluorescent protein (GFP) and RPN1 was prepared. Specifically, to induce rapid lysis of a human RPN1 protein, a wild type RPN1 polynucleotide (SEQ ID NO: 2) encoding a wild type human RPN1 protein (SEQ ID NO: 1) was used to prepare a mutant RPN-$I^{N299T}$ polynucleotide (SEQ ID NO: 4) encoding a mutant RPN-$I^{N299T}$ protein (SEQ ID NO: 3). The mutant RPN-$I^{N299T}$ polynucleotide (SEQ ID NO: 4) was cloned into a pEGFP-C1 plasmid vector (Clontech Laboratories Inc.) to prepare a pEGFP-RPN1$^{N299T}$ plasmid which enables expression of a fusion protein including a GFP protein and the RPN1$^{N299T}$ protein.

On the other hand, a plasmid vector expressing a red fluorescent protein (RFP) as a ubiquitin-proteasome-independent protein which is not lysed by a ubiquitin-proteasome was prepared. Specifically, a pDs-Red2-Express-N1 plasmid vector (Clontech Laboratories Inc.) which enables expression of a *Discosoma* species RFP (DsRed) was prepared.

1.2 Verification of Plasmid Vector Introduction to Cells

As host cells, human embryonic kidney (HEK) 293T cells were cultured in a DMEM (Dulbecco's Modified Eagle's Medium) (Gibco/BRL) including 10% (v/v) fetal bovine serum (FBS) and 1% (v/v) penicillin-streptomycin (Gibco/BRL) at a temperature of 37° C. under the atmosphere of 5% $CO_2$. During the culturing, the medium was replaced with new medium every second day.

$2 \times 10^6$ of the cultured cells were transferred to a 100 mm dish, and 5 μg of the GFP-RPN1 plasmid vector or 5 μg of the DsRed plasmid vector prepared as described in Example 1.1 was respectively added to the transferred cells and transfected in the cells by calcium phosphate transfection. Then, the transfected cells were cultured in a fresh medium for 24 hours.

Figure 2A:
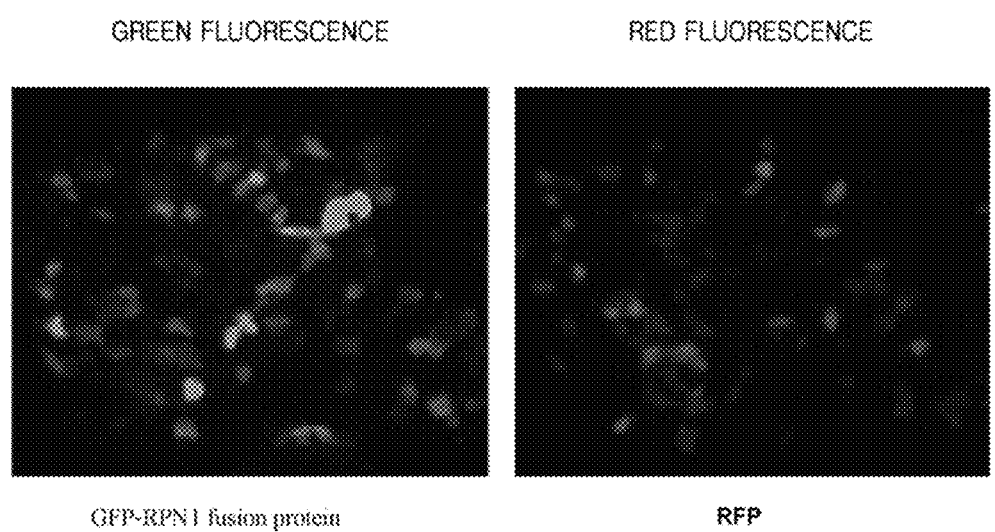
FIG. 2a is a microscopic image of the expression of a green fluorescent protein-ribophorin I (GFP-RPN1) fusion protein and a red fluorescent protein (RFP) (left: green fluorescence image; right: red fluorescence image)

Afterward, the expression of the GFP-RPN1 fusion protein or the RFP was verified by using a fluorescence microscope (Nikon). The result is shown in FIG. 2a (left: green fluorescence; right: red fluorescence).

The cultured cells were obtained, and 200 μl of Tris-EDTA lysis buffer including 50 mM Tris-Cl (USB, Cleveland, Ohio, USA), pH 7.4, 150 mM NaCl (USB, Cleveland, Ohio, USA), 2 mM EDTA (Sigma), 0.5% NP-40 (Sigma), protease inhibitor cocktail (Roche), and 1 mM sodium orthovanadate (Sigma) was added to the obtained cells. The resulting solution was vortexed, and then centrifuged at 4° C. and 12000 rpm to obtain the supernatant.

200 μl of the obtained supernatant was analyzed by using a capillary electrophoresis system including dual laser-induced fluorescence (LIF) detectors (dual LIF CE system). The used capillary electrophoresis system was an 800 plus CE system (Beckman coulter, Fullerton, Calif., USA). The LIF detectors were a Beckman P/ACE System Laser Module 488 and a Laser Module 635 having respective excitation wavelengths of 488 nm and 635 nm and respective emission wavelengths of 520 nm and 663 nm. The separating was performed by using 100 mM Tris-CHES (Sigma) and 3.5 mM sodium dodecyl sulfate (SDS) (pH 9.0) (Bio-Rad). The capillary electrophoresis was performed by using an uncoated capillary (Beckman Coulter) having an inner diameter of 50 µm and a length of 30 cm at voltage of 18 kV. Sample injection was performed at the pressure of 0.5 psi for five seconds. The results of the capillary electrophoresis at the excitation wavelengths of 488 nm and 635 nm are respectively shown in FIG. 2b (x-axis: time (min); y-axis: relative fluorescence unit (RFU); left: excitation wavelength 488 nm; and right: excitation wavelength 635 nm). Since the excitation wavelengths of the GFP and RFP were 488 nm and 635 nm, respectively, the left of FIG. 2b is the graph of the GFP-RPN1 fusion protein, and the right of FIG. 2b is the graph of the RFP.

On the other hand, a capillary electrophoresis was performed with 50 µl of the obtained supernatant, and an immunoblotting was performed with an anti-GFP antibody (Santa Cruz Biotechnology) and an anti-Ds-Red antibody (Clontech Laboratories Inc.). Cells which are not transfected were used as a negative control group. The result of the immunoblotting is shown in FIG. 2c (Lane 1: negative control group; Lane 2: transfected cells).

Figure 2B:
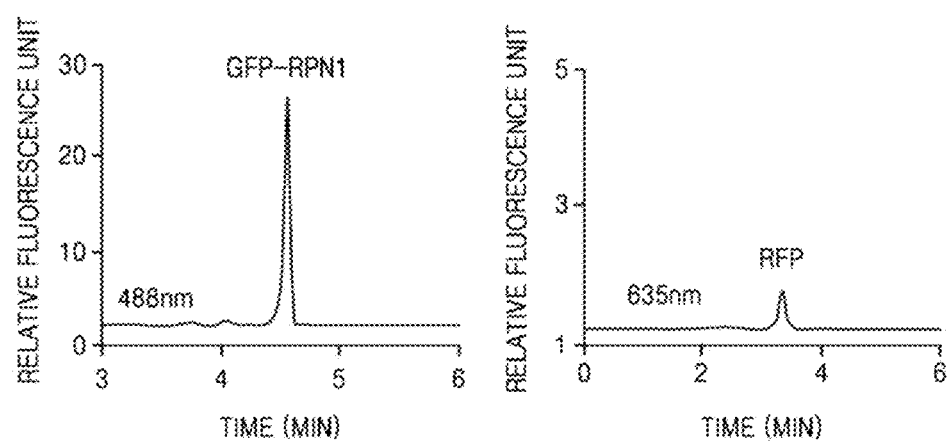
FIG. 2b is a graph showing the results of capillary electrophoresis performed at the excitation wavelengths of 488 nm and 635 nm (x-axis: time (min); y-axis: relative fluorescence unit (RFU); left: excitation wavelength 488 nm; and right: excitation wavelength 635 nm)
Figure 2C:
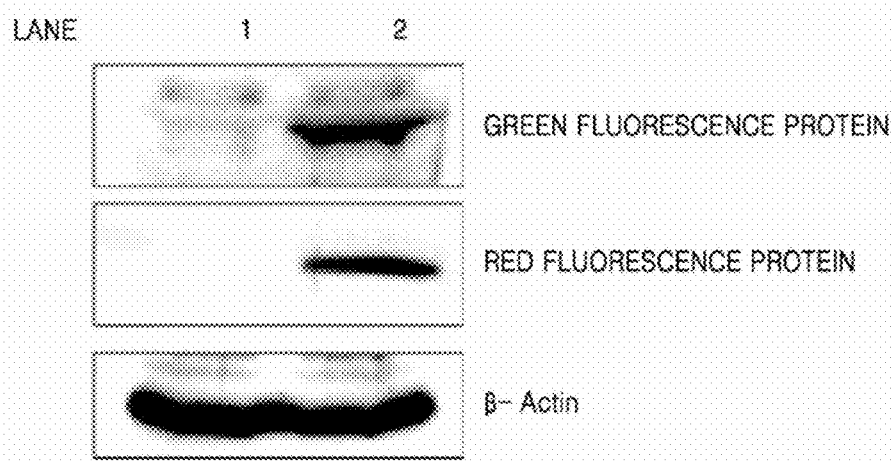
FIG. 2c is an image obtained by immunoblotting which was performed by using an anti-GFP antibody and an anti-Ds-Red antibody (Lane 1: negative control group; Lane 2: transfected cells)

Therefore, as shown in FIGS. 2a to 2c, the intracellular expression of the GFP-RPN1 fusion protein and the RFP was verified.

1.3 Condition Set-Up of Capillary Electrophoresis System Including Dual LIF Detectors (Dual LIF CE System)

In the capillary electrophoresis, the separation conditions according to the inner diameter and length of the capillary, and electrophoresis conditions were verified.

Figure 3A:
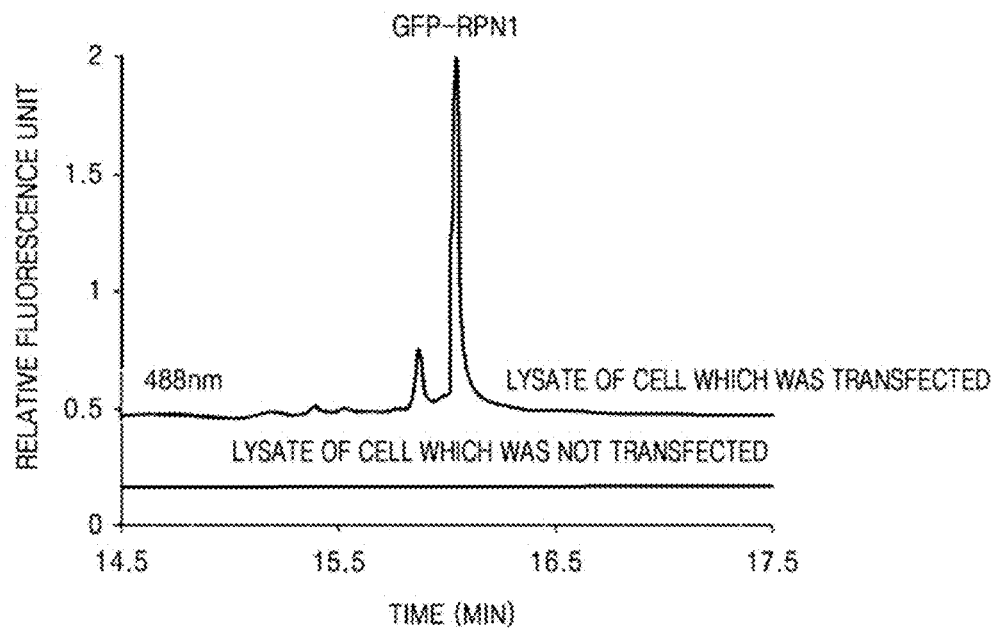
FIGS. 3a to 3b are graphs showing the results of capillary electrophoresis performed by using an uncoated capillary having an inner diameter of 50 μm and a length of 30 cm or an uncoated capillary having an inner diameter of 75 μm and a length of 50 cm, respectively (x-axis: time (min); y-axis: relative fluorescence unit (RFU))
Figure 3B:
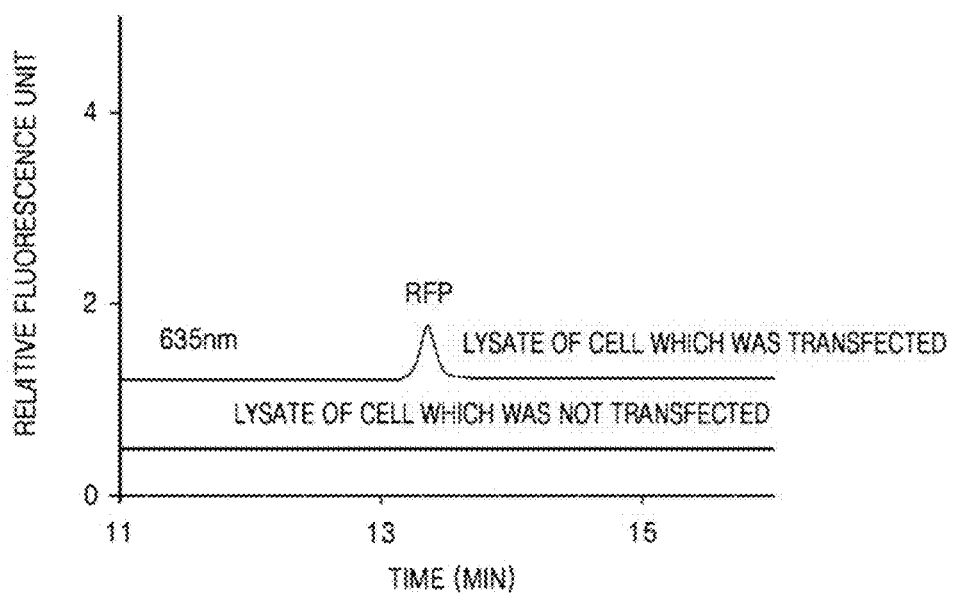

The capillary electrophoresis was performed with the cell extract obtained in Example 1.2 by using an uncoated capillary having an inner diameter of 50 µm and a length of 30 cm or an uncoated capillary having an inner diameter of 75 µm and a length of 50 cm, and the results of the verified peaks of the separated fluorescent proteins are shown in FIG. 3a and FIG. 3b, respectively.

In addition, the capillary electrophoresis was performed by varying the SDS concentration from about 3 mM to about 20 mM or by varying the pH of the running buffer from about pH 6 to about pH 11, and the peaks were compared.

The results showed that the GFP-RPN1 fusion protein, which was a ubiquitin proteasome-dependent substrate, was best separated and showed the highest peaks when the capillary electrophoresis was performed under the electrophoresis conditions of 100 mM Tris-CHES and 10 mM SDS (pH 9.0) by using an uncoated capillary having an inner diameter of 75 µm and a length of 50 cm.

EXAMPLE 2

Quantification of Ubiquitin-Proteasome-Dependent Protein Degradation

An EGFP-RPN1 plasmid vector and a DsRed plasmid vector were prepared as described in Example 1.1, and HEK 293T cells were prepared as described in Example 1.2.

$2 \times 10^6$ of the HEK 293T cells were transferred to a 100 mm dish, and 5 µg, 2 µg, or 0.2 µg of the EGFP-RPN1 plasmid vector and 5 µg of the DsRed plasmid vector were respectively added to the culture solution. Then, the resulting culture solution was incubated for 24 hours. Afterward, 10 µM of the proteasome inhibitor MG132 (A. G. Science) was added to the culture solution which was then incubated for two hours to induce intracellular accumulation of the GFP-RPN1 fusion protein. Subsequently, 100 µg/ml of cycloheximide (Sigma), which is a protein synthesis inhibitor, was added to the culture solution. Then, protein lysis was induced by incubating the culture solution for 0 hours (immediately after adding cycloheximide), 0.5 hours, 1 hour, 3 hours, or 5 hours. Then, the supernatant which was the cell lysate was obtained as described in Example 1.2.

Figure 4A:
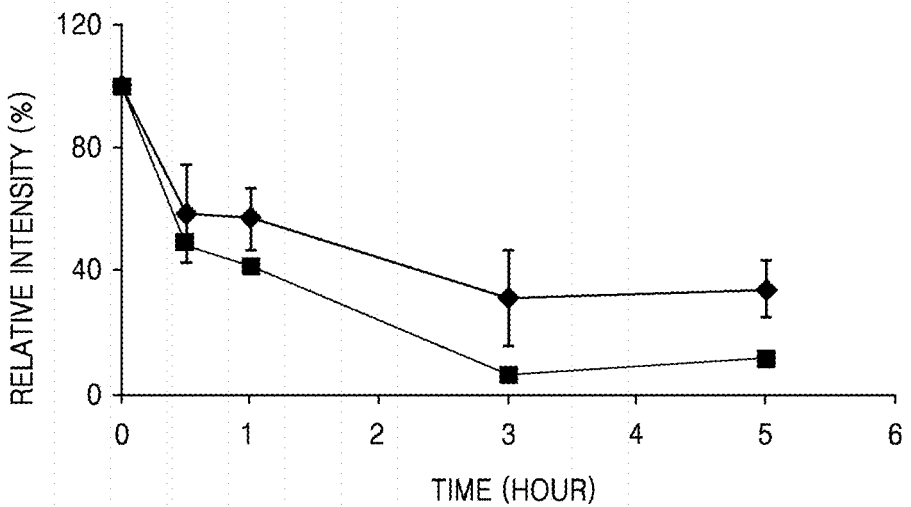
FIGS. 4a to 4c are graphs showing the intensity results quantified by using the dual LIF CE system and the immunoblotting method are shown in FIGS. 4a to 4c (x-axis: time (hour); y-axis: quantified relative intensity (%); ♦: dual LIF CE system; and ■: immunoblotting)
Figure 4B:
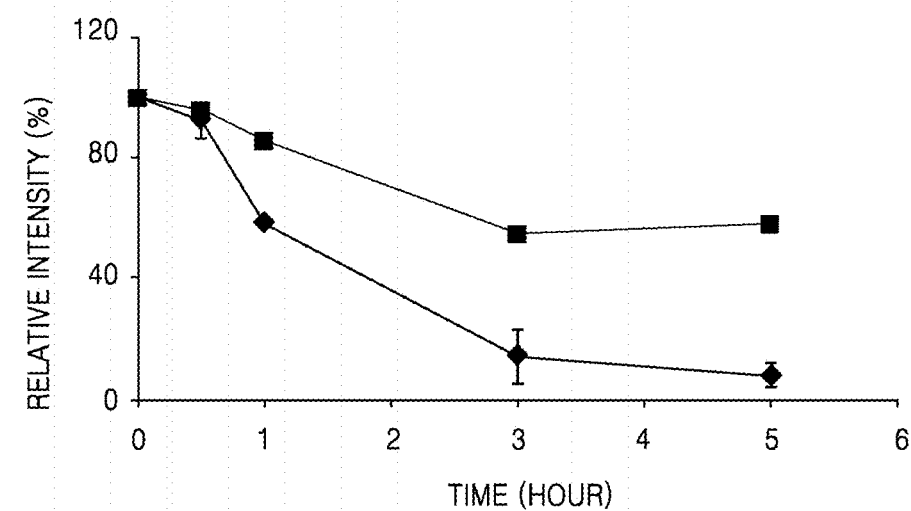
Figure 4C:
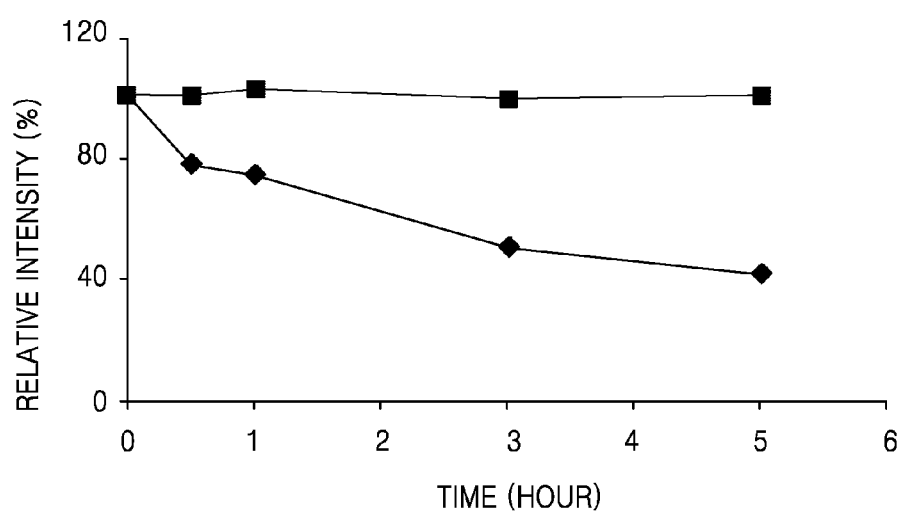

As described in Example 1.3, a capillary electrophoresis was performed with the obtained supernatant under the electrophoresis conditions of 100 mM Tris-CHES and 10 mM SDS (pH 9.0) by using a dual LIF CE system including an uncoated capillary having an inner diameter of 75 µm and a length of 50 cm to quantify the peak height. In addition, to compare the detection sensitivity of the capillary electrophoresis system including dual LIF detectors, the fluorescence intensity of the bands obtained by immunoblotting which was performed by the method described in Example 1.2 was quantified. The quantified values of the GFP-RPN1 fusion protein were divided by the quantified values of the RFP to correct the transfection efficiency. The fluorescence intensity results quantified by using the dual LIF CE system and the immunoblotting method are shown in FIGS. 4a to 4c (x-axis: time (hour); y-axis: quantified relative intensity (%); ♦: dual LIF CE system; and ■: immunoblotting). FIG. 4a is a graph showing the result obtained by transfecting 5 µg of EGFP-RPN1 plasmid vector and 5 µg of DsRed plasmid vector, FIG. 4b is a graph showing the result obtained by transfecting 2 µg of EGFP-RPN1 plasmid vector and 5 µg of DsRed plasmid vector, and FIG. 4c is a graph showing the result obtained by transfecting 0.2 µg of EGFP-RPN1 plasmid vector and 5 µg of DsRed plasmid vector.

As shown in FIGS. 4a to 4c, the dual LIF CE system allows quantitative measurement in all the cases where 5 µg, 2 µg, and 0.2 µg of the EGFP-RPN1 plasmid vector was added respectively, but the GFP-RPN1 expression at a low concentration was not quantified by immunoblotting. Therefore, it was verified that the dual LIF CE system may be used to detect an extremely small amount of DNA introduced to cells.

EXAMPLE 3

Quantification of Proteins Accumulated by Proteasome Inhibitor

To verify the amount of proteins accumulated intracellularly according to the kinds of proteasome inhibitors, MG132 was used as a proteasome inhibitor, and bortezomib and carfilzomib, which are both a proteasome inhibitor and an anticancer agent, were used.

An EGFP-RPN1 plasmid vector and a DsRed plasmid vector were prepared as described in Example 1.1, and HEK 293T cells were prepared as described in Example 1.2.

$2 \times 10^6$ of the HEK 293T cells were transferred to a 100 mm dish, and 5 µg of the EGFP-RPN1 plasmid vector and 5 µg of the DsRed plasmid vector were added to the culture solution. Then, the resulting culture solution was incubated for 24 hours. Afterward, from about 0 to about 20 µM of MG132 (A. G. Science), bortezomib (LC Laboratories), and carfilzomib (LC Laboratories) were added to the culture solution which was then incubated for two hours to induce intracellular accumulation of proteins.

Subsequently, the supernatant which was the cell lysate was obtained as described in Example 1.2. As described in Example 1.3, a capillary electrophoresis was performed with the obtained supernatant under the electrophoresis conditions of 100 mM Tris-CHES and 10 mM SDS (pH 9.0) by using a dual LIF CE system including an uncoated capillary having an inner diameter of 75 μm and a length of 50 cm to quantify the peak height. The relative intensity (%) of the peaks according to the concentrations (μM) of MG132, bortezomib, and carfilzomib is respectively shown in FIGS. 5a to 5c.

Figure 5A:
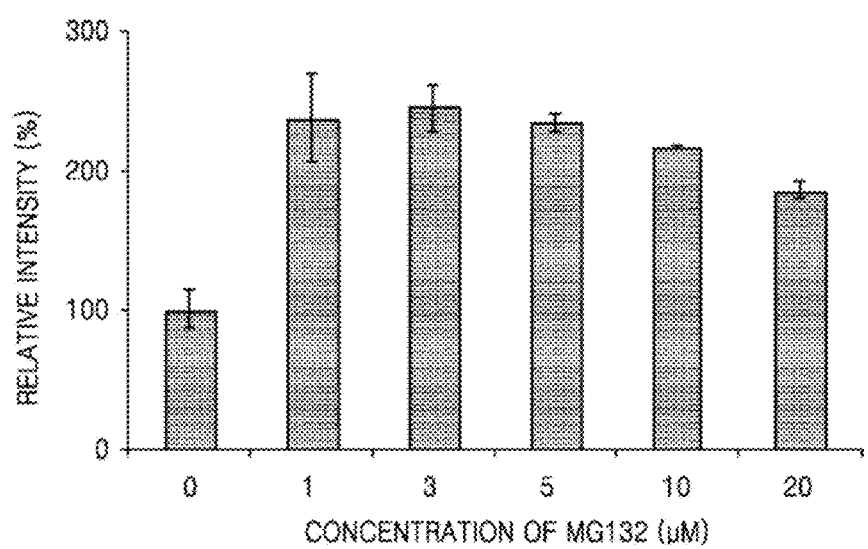
FIGS. 5a to 5c are graphs showing the relative intensity (%) of the peaks according to the concentrations (μM) of MG132, bortezomib, and carfilzomib, respectively.
Figure 5B:
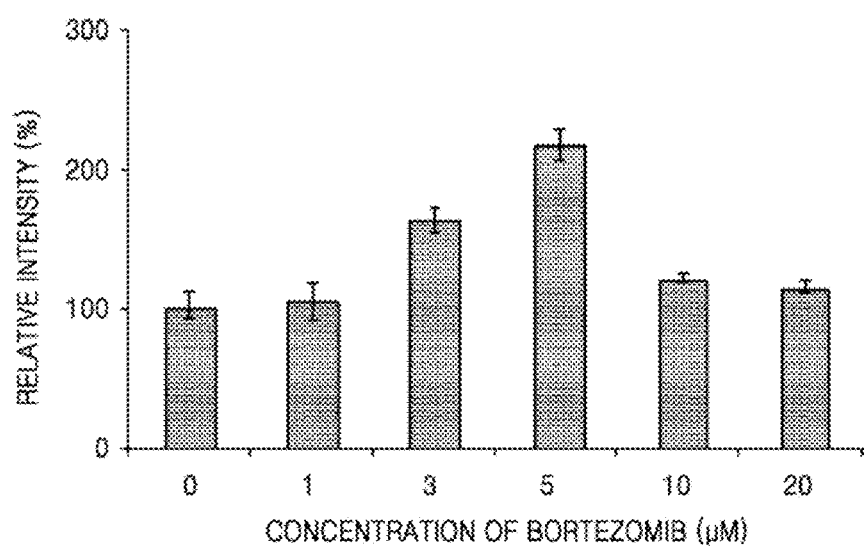
Figure 5C:
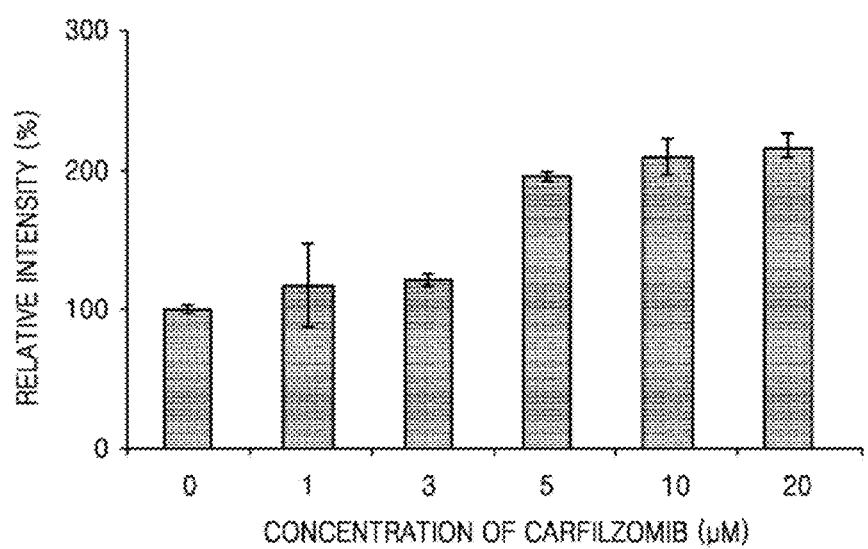

As shown in FIGS. 5a to 5c, the amount of the accumulated proteins was varied according to the increase of the concentrations of MG132, bortezomib, and carfilzomib, and the variation pattern could be detected in a short period of time by using the dual LIF CE system.

As described above, according to the method of quantitatively analyzing ubiquitin-proteasome with respect to a target polypeptide according to one aspect of the present invention, the pattern of lysis of a target polypeptide by a ubiquitin-proteasome in target cells may be quantitatively analyzed in a rapid and highly sensitive way. In addition, according to the method of screening a ubiquitin-proteasome inhibitor according to another aspect of the present invention, a ubiquitin-proteasome inhibitor may be screened in a rapid and highly sensitive way, and an anticancer agent and the activity thereof may be rapidly screened.

What is claimed is:

1. An in vitro method of rapidly, quantitatively analyzing ubiquitin proteasome activity with respect to a target polypeptide, the method comprising:
   simultaneously or sequentially adding a first polynucleotide encoding a fusion protein comprising a target polypeptide and a first fluorescent protein, and a second polynucleotide encoding a second fluorescent protein to a culture solution comprising cells to simultaneously or sequentially introduce the first polynucleotide and the second polynucleotide to the cells,
   wherein the first fluorescent protein or the second fluorescent protein is not degraded by the ubiquitin-proteasome activity;
   obtaining cells from the culture solution and lysing the obtained cells to obtain cell lysis solution;
   separating the obtained cell lysis solution by capillary electrophoresis and simultaneously or sequentially quantifying fluorescence intensity of the fusion protein comprising the target polypeptide and the first fluorescent protein, and fluorescence intensity of the second fluorescent protein by using a dual fluorescence detector; and
   analyzing the fluorescence intensity of the fusion protein comprising the target polypeptide and the first fluorescent protein relative to the fluorescence intensity of the second fluorescent protein to rapidly quantify intracellular degradation of the target polypeptide by the ubiquitin-proteasome activity.

2. The method of claim 1, wherein the first fluorescent protein and the second fluorescent protein emit light of different wavelengths.

3. The method of claim 1, wherein the first fluorescent protein is a green fluorescent protein.

4. The method of claim 1, wherein the second fluorescent protein is a red fluorescent protein.

5. The method of claim 1, wherein the cells are cells comprising a mutated ubiquitin or a mutated proteasome.

6. The method of claim 1, wherein the cells are cancer cells, neurons, cardiac myocytes, or immunocytes.

7. The method of claim 1, wherein the method further comprises analyzing variation of the intracellular degradation of the target polypeptide to quantitatively analyze variation of ubiquitin-proteasome activity with respect to the target polypeptide.

8. An in vitro method of rapidly screening an ubiquitin proteasome inhibitor, the method comprising:
   simultaneously or sequentially adding a first polynucleotide encoding a fusion protein comprising a target polypeptide, which is degraded by a ubiquitin-proteasome inhibitor and a first fluorescent protein, and a second polynucleotide encoding a second fluorescent protein to a culture solution comprising cells to simultaneously or sequentially introduce the first polynucleotide and the second polynucleotide to the cells,
   wherein the first fluorescent protein or the second fluorescent protein is not degraded by a ubiquitin-proteasome inhibitor;
   adding an ubiquitin-proteasome inhibitor candidate substance to the culture solution;
   obtaining cells from the culture solution and lysing the obtained cells to obtain cell lysis solution;
   separating the obtained cell lysis solution by capillary electrophoresis and simultaneously or sequentially quantifying fluorescence intensity of the fusion protein comprising the target polypeptide and the first fluorescent protein, and fluorescence intensity of the second fluorescent protein by using a dual fluorescence detector; and
   comparing the fluorescence intensity of the fusion protein comprising the target polypeptide and the first fluorescent protein relative to the fluorescence intensity of the second fluorescent protein with fluorescence intensity of a negative control group to which an ubiquitin-proteasome inhibitor candidate substance is not added to rapidly screen a ubiquitin-proteasome inhibitor.

9. The method of claim 8, wherein the first fluorescent protein and the second fluorescent protein emit light of different wavelengths.

10. The method of claim 8, wherein the first fluorescent protein is a green fluorescent protein.

11. The method of claim 8, wherein the second fluorescent protein is a red fluorescent protein.

12. The method of claim 8, wherein the cells are cells comprising a mutated ubiquitin or a mutated proteasome.

13. The method of claim 8, wherein the ubiquitin-proteasome inhibitor is a candidate substance for treating a cancer, a degenerative brain disease, a cardiovascular disease, an autoimmune disease, or a combination thereof.

14. The method of claim 8, wherein the method further comprises analyzing variation of intracellular degradation of the target polypeptide to quantitatively analyze variation of ubiquitin-proteasome activity with respect to the ubiquitin-proteasome inhibitor candidate substance.

* * * * *

SEQUENCE LISTING

```
<160> NUMBER OF SEQ ID NOS: 4

<210> SEQ ID NO 1
<211> LENGTH: 607
<212> TYPE: PRT
<213> ORGANISM: Artificial Sequence
<220> FEATURE:
<223> OTHER INFORMATION: wildtype human ribophorin I

<400> SEQUENCE: 1

Met Glu Ala Pro Ala Ala Gly Leu Phe Leu Leu Leu Leu Gly Thr
 1               5                  10                  15

Trp Ala Pro Ala Pro Gly Ser Ala Ser Ser Glu Ala Pro Pro Leu Ile
                20                  25                  30

Asn Glu Asp Val Lys Arg Thr Val Asp Leu Ser Ser His Leu Ala Lys
            35                  40                  45

Val Thr Ala Glu Val Val Leu Ala His Leu Gly Gly Gly Ser Thr Ser
        50                  55                  60

Arg Ala Thr Ser Phe Leu Leu Ala Leu Glu Pro Glu Leu Glu Ala Arg
    65                  70                  75                  80

Leu Ala His Leu Gly Val Gln Val Lys Gly Glu Asp Glu Glu Glu Asn
                85                  90                  95

Asn Leu Glu Val Arg Glu Thr Lys Ile Lys Gly Lys Ser Gly Arg Phe
            100                 105                 110

Phe Thr Val Lys Leu Pro Val Ala Leu Asp Pro Gly Ala Lys Ile Ser
        115                 120                 125

Val Ile Val Glu Thr Val Tyr Thr His Val Leu His Pro Tyr Pro Thr
    130                 135                 140

Gln Ile Thr Gln Ser Glu Lys Gln Phe Val Val Phe Glu Gly Asn His
145                 150                 155                 160

Tyr Phe Tyr Ser Pro Tyr Pro Thr Lys Thr Gln Thr Met Arg Val Lys
                165                 170                 175

Leu Ala Ser Arg Asn Val Glu Ser Tyr Thr Lys Leu Gly Asn Pro Thr
            180                 185                 190

Arg Ser Glu Asp Leu Leu Asp Tyr Gly Pro Phe Arg Asp Val Pro Ala
        195                 200                 205

Tyr Ser Gln Asp Thr Phe Lys Val His Tyr Glu Asn Asn Ser Pro Phe
    210                 215                 220

Leu Thr Ile Thr Ser Met Thr Arg Val Ile Glu Val Ser His Trp Gly
225                 230                 235                 240

Asn Ile Ala Val Glu Glu Asn Val Asp Leu Lys His Thr Gly Ala Val
                245                 250                 255

Leu Lys Gly Pro Phe Ser Arg Tyr Asp Tyr Gln Arg Gln Pro Asp Ser
            260                 265                 270
```

```
Gly Ile Ser Ser Ile Arg Ser Phe Lys Thr Ile Leu Pro Ala Ala Ala
            275                 280                 285

Gln Asp Val Tyr Tyr Arg Asp Glu Ile Gly Asn Val Ser Thr Ser His
        290                 295                 300

Leu Leu Ile Leu Asp Asp Ser Val Glu Met Glu Ile Arg Pro Arg Phe
305                 310                 315                 320

Pro Leu Phe Gly Gly Trp Lys Thr His Tyr Ile Val Gly Tyr Asn Leu
                325                 330                 335

Pro Ser Tyr Glu Tyr Leu Tyr Asn Leu Gly Asp Gln Tyr Ala Leu Lys
            340                 345                 350

Met Arg Phe Val Asp His Val Phe Asp Glu Gln Val Ile Asp Ser Leu
        355                 360                 365

Thr Val Lys Ile Ile Leu Pro Glu Gly Ala Lys Asn Ile Glu Ile Asp
370                 375                 380

Ser Pro Tyr Glu Ile Ser Arg Ala Pro Asp Glu Leu His Tyr Thr Tyr
385                 390                 395                 400

Leu Asp Thr Phe Gly Arg Pro Val Ile Val Ala Tyr Lys Lys Asn Leu
                405                 410                 415

Val Glu Gln His Ile Gln Asp Ile Val Val His Tyr Thr Phe Asn Lys
            420                 425                 430

Val Leu Met Leu Gln Glu Pro Leu Leu Val Val Ala Ala Phe Tyr Ile
        435                 440                 445

Leu Phe Phe Thr Val Ile Ile Tyr Val Arg Leu Asp Phe Ser Ile Thr
450                 455                 460

Lys Asp Pro Ala Ala Glu Ala Arg Met Lys Val Ala Cys Ile Thr Glu
465                 470                 475                 480

Gln Val Leu Thr Leu Val Asn Lys Arg Ile Gly Leu Tyr Arg His Phe
                485                 490                 495

Asp Glu Thr Val Asn Arg Tyr Lys Gln Ser Arg Asp Ile Ser Thr Leu
            500                 505                 510

Asn Ser Gly Lys Lys Ser Leu Glu Thr Glu His Lys Ala Leu Thr Ser
        515                 520                 525

Glu Ile Ala Leu Leu Gln Ser Arg Leu Lys Thr Glu Gly Ser Asp Leu
530                 535                 540

Cys Asp Arg Val Ser Glu Met Gln Lys Leu Asp Ala Gln Val Lys Glu
545                 550                 555                 560

Leu Val Leu Lys Ser Ala Val Glu Ala Glu Arg Leu Val Ala Gly Lys
                565                 570                 575

Leu Lys Lys Asp Thr Tyr Ile Asp Asn Glu Lys Leu Ile Ser Gly Lys
            580                 585                 590

Arg Gln Glu Leu Val Thr Lys Ile Asp His Ile Leu Asp Ala Leu
        595                 600                 605

<210> SEQ ID NO 2
<211> LENGTH: 1824
<212> TYPE: DNA
<213> ORGANISM: Artificial Sequence
<220> FEATURE:
<223> OTHER INFORMATION: wildtype human ribophorin I

<400> SEQUENCE: 2
atggaggcgc cagccgccgg cttgtttctg ctcctgttgc ttgggacttg ggccccggcg    60
ccgggcagcg cctcctccga ggcaccgccg ctgatcaatg aggacgtgaa gcgcacagtg   120
gacctaagca gccacctggc taaggtgacg gccgaggtgg tcctggcgca cctgggcggc   180
```

-continued

```
ggctccacgt cccgagctac ctctttcctg ctggctttgg agcctgagct cgaggcccgg    240
ctggcgcacc tgggcgtgca ggtaaaggga gaagatgagg aagagaacaa tttggaagta    300
cgtgaaacca aaattaaggg taaaagtggg agattcttca cagtcaagct cccagttgct    360
cttgatcctg gggccaagat ttcagtcatt gtggaaacag tctacaccca tgtgcttcat    420
ccatatccaa cccagatcac ccagtcagag aaacagtttg tggtgtttga ggggaaccat    480
tatttctact ctccctatcc aacgaagaca caaaccatgc gtgtgaagct tgcctctcga    540
aatgtggaga gctacaccaa gctggggaac cccacgcgct ctgaggacct actggattat    600 gggccttttca gagatgtgcc tgcctatagt caggatactt ttaaagtaca ttatgagaac    660
aacagccctt tcctgaccat caccagcatg acccgagtca ttgaagtctc tcactggggt    720
aatattgctg tggaagaaaa tgtggactta agcacacag gagctgtgct taaggggcct    780
ttctcacgct atgattacca gagacagcca gatagtggaa tatcctccat ccgttctttt    840
aagaccatcc ttcctgctgc tgcccaggat gtttattacc gggatgagat tggcaatgtt    900
tctaccagcc acctccttat tttggatgac tctgtagaga tggaaatccg gcctcgcttc    960
cctctctttg gcgggtggaa gacccattac atcgttggct acaacctccc aagctatgag    1020
tacctctata atttgggtga ccagtatgca ctgaagatga ggtttgtgga ccatgtgttt    1080
gatgaacaag tgatagattc tctgactgtg aagatcatcc tgcctgaagg agccaagaac    1140
attgaaattg atagtcccta tgaaatcagc cgtgccccag atgagctgca ctacacctat    1200
ctggatacat ttggccgccc tgtgattgtt gcctacaaga aaaatctggt agaacagcac    1260
attcaggaca ttgtggtcca ctacacgttc aacaaggtgc tcatgctgca ggagcccctg    1320
ctggtggtgg cggccttcta catcctgttc ttcaccgtta tcatctatgt tcggctggac    1380
ttctccatca ccaaggatcc agccgcagaa gccaggatga aggtagcctg catcacagag    1440
caggtcttga ccctggtcaa caagagaata ggcctttacc gtcactttga cgagaccgtc    1500
aataggtaca agcaatcccg ggacatctcc acccctcaaca gtggcaagaa gagcctggag    1560
actgaacaca aggccttgac cagtgagatt gcactgctgc agtccaggct gaagacagag    1620
ggctctgatc tgtgcgacag agtgagcgaa atgcagaagc tggatgcaca ggtcaaggag    1680
ctggtgctga agtcggcggt ggaggctgag cgcctggtgg ctggcaagct caagaaagac    1740
acgtacattg agaatgagaa gctcatctca ggaaagcgcc aggagctggt caccaagatc    1800
gaccacatcc tggatgccct gtag                                           1824
```

<210> SEQ ID NO 3
<211> LENGTH: 607
<212> TYPE: PRT
<213> ORGANISM: Artificial Sequence
<220> FEATURE:
<223> OTHER INFORMATION: mutant human ribophorin I(N299T)

<400> SEQUENCE: 3

```
Met Glu Ala Pro Ala Ala Gly Leu Phe Leu Leu Leu Leu Gly Thr
 1               5                  10                  15

Trp Ala Pro Ala Pro Gly Ser Ala Ser Ser Glu Ala Pro Pro Leu Ile
            20                  25                  30

Asn Glu Asp Val Lys Arg Thr Val Asp Leu Ser Ser His Leu Ala Lys
        35                  40                  45

Val Thr Ala Glu Val Val Leu Ala His Leu Gly Gly Gly Ser Thr Ser
    50                  55                  60

Arg Ala Thr Ser Phe Leu Leu Ala Leu Glu Pro Glu Leu Glu Ala Arg
```

-continued

```
                65                  70                  75                  80
Leu Ala His Leu Gly Val Gln Val Lys Gly Glu Asp Glu Glu Glu Asn
                    85                  90                  95

Asn Leu Glu Val Arg Glu Thr Lys Ile Lys Gly Lys Ser Gly Arg Phe
                    100                 105                 110

Phe Thr Val Lys Leu Pro Val Ala Leu Asp Pro Gly Ala Lys Ile Ser
                    115                 120                 125

Val Ile Val Glu Thr Val Tyr Thr His Val Leu His Pro Tyr Pro Thr
            130                 135                 140

Gln Ile Thr Gln Ser Glu Lys Gln Phe Val Val Phe Glu Gly Asn His
145                 150                 155                 160

Tyr Phe Tyr Ser Pro Tyr Pro Thr Lys Thr Gln Thr Met Arg Val Lys
                165                 170                 175

Leu Ala Ser Arg Asn Val Glu Ser Tyr Thr Lys Leu Gly Asn Pro Thr
                180                 185                 190

Arg Ser Glu Asp Leu Leu Asp Tyr Gly Pro Phe Arg Asp Val Pro Ala
                195                 200                 205

Tyr Ser Gln Asp Thr Phe Lys Val His Tyr Glu Asn Asn Ser Pro Phe
            210                 215                 220

Leu Thr Ile Thr Ser Met Thr Arg Val Ile Glu Val Ser His Trp Gly
225                 230                 235                 240

Asn Ile Ala Val Glu Glu Asn Val Asp Leu Lys His Thr Gly Ala Val
                245                 250                 255

Leu Lys Gly Pro Phe Ser Arg Tyr Asp Tyr Gln Arg Gln Pro Asp Ser
                260                 265                 270

Gly Ile Ser Ser Ile Arg Ser Phe Lys Thr Ile Leu Pro Ala Ala Ala
            275                 280                 285

Gln Asp Val Tyr Tyr Arg Asp Glu Ile Gly Thr Val Ser Thr Ser His
            290                 295                 300

Leu Leu Ile Leu Asp Asp Ser Val Glu Met Glu Ile Arg Pro Arg Phe
305                 310                 315                 320

Pro Leu Phe Gly Gly Trp Lys Thr His Tyr Ile Val Gly Tyr Asn Leu
                325                 330                 335

Pro Ser Tyr Glu Tyr Leu Tyr Asn Leu Gly Asp Gln Tyr Ala Leu Lys
                340                 345                 350

Met Arg Phe Val Asp His Val Phe Asp Glu Gln Val Ile Asp Ser Leu
                355                 360                 365

Thr Val Lys Ile Ile Leu Pro Glu Gly Ala Lys Asn Ile Glu Ile Asp
        370                 375                 380

Ser Pro Tyr Glu Ile Ser Arg Ala Pro Asp Glu Leu His Tyr Thr Tyr
385                 390                 395                 400

Leu Asp Thr Phe Gly Arg Pro Val Ile Val Ala Tyr Lys Lys Asn Leu
                405                 410                 415

Val Glu Gln His Ile Gln Asp Ile Val Val His Tyr Thr Phe Asn Lys
                420                 425                 430

Val Leu Met Leu Gln Glu Pro Leu Leu Val Val Ala Ala Phe Tyr Ile
            435                 440                 445

Leu Phe Phe Thr Val Ile Ile Tyr Val Arg Leu Asp Phe Ser Ile Thr
            450                 455                 460

Lys Asp Pro Ala Ala Glu Ala Arg Met Lys Val Ala Cys Ile Thr Glu
465                 470                 475                 480

Gln Val Leu Thr Leu Val Asn Lys Arg Ile Gly Leu Tyr Arg His Phe
                485                 490                 495
```

```
Asp Glu Thr Val Asn Arg Tyr Lys Gln Ser Arg Asp Ile Ser Thr Leu
            500                 505                 510

Asn Ser Gly Lys Lys Ser Leu Glu Thr Glu His Lys Ala Leu Thr Ser
        515                 520                 525

Glu Ile Ala Leu Leu Gln Ser Arg Leu Lys Thr Glu Gly Ser Asp Leu
    530                 535                 540

Cys Asp Arg Val Ser Glu Met Gln Lys Leu Asp Ala Gln Val Lys Glu
545                 550                 555                 560

Leu Val Leu Lys Ser Ala Val Glu Ala Glu Arg Leu Val Ala Gly Lys
                565                 570                 575

Leu Lys Lys Asp Thr Tyr Ile Glu Asn Glu Lys Leu Ile Ser Gly Lys
            580                 585                 590

Arg Gln Glu Leu Val Thr Lys Ile Asp His Ile Leu Asp Ala Leu
        595                 600                 605
```

<210> SEQ ID NO 4
<211> LENGTH: 1824
<212> TYPE: DNA
<213> ORGANISM: Artificial Sequence
<220> FEATURE:
<223> OTHER INFORMATION: mutant human ribophorin I(N299T)

<400> SEQUENCE: 4

```
atggaggcgc cagccgccgg cttgtttctg ctcctgttgc ttgggacttg ggccccggcg      60
ccgggcagcg cctcctccga ggcaccgccg ctgatcaatg aggacgtgaa gcgcacagtg     120
gacctaagca gccacctggc taaggtgacg gccgaggtgg tcctggcgca cctgggcggc     180
ggctccacgt cccgagctac ctctttcctg ctggctttgg agcctgagct cgaggcccgg     240
ctggcgcacc tgggcgtgca ggtaaaggga gaagatgagg aagagaacaa tttggaagta     300
cgtgaaacca aaattaaggg taaaagtggg agattcttca cagtcaagct cccagttgct     360
cttgatcctg ggccaagat ttcagtcatt gtggaaacag tctacaccca tgtgcttcat      420
ccatatccaa cccagatcac ccagtcagag aaacagtttg tggtgtttga ggggaaccat     480
tatttctact ctccctatcc aacgaagaca caaaccatgc gtgtgaagct tgcctctcga     540
aatgtggaga gctacaccaa gctggggaac cccacgcgct ctgaggacct actggattat     600
gggcctttca gagatgtgcc tgcctatagt caggatactt taaagtaca ttatgagaac      660
aacagccctt tcctgaccat caccagcatg acccgagtca ttgaagtctc tcactggggt     720
atattgctg tggaagaaaa tgtggactta agcacacag gagctgtgct taaggggcct       780
ttctcacgct atgattacca gagacagcca gatagtggaa tatcctccat ccgttctttt     840
aagaccatcc ttcctgctgc tgcccaggat gtttattacc gggatgagat tggcacggtt     900
tctaccagcc acctccttat tttggatgac tctgtagaga tggaaatccg gcctcgcttc     960
cctctctttg gcgggtggaa gacccattac atcgttggct acaacctccc aagctatgag    1020
tacctctata atttgggtga ccagtatgca ctgaagatga ggtttgtgga ccatgtgttt    1080
gatgaacaag tgatagattc tctgactgtg aagatcatcc tgcctgaagg agccaagaac    1140
attgaaattg atagtcccta tgaaatcagc cgtgccccag atgagctgca ctacacctat    1200
ctggatacat ttggccgccc tgtgattgtt gcctacaaga aaaatctggt agaacagcac    1260
attcaggaca ttgtggtcca ctacacgttc aacaaggtgc tcatgctgca ggagcccctg    1320
ctggtggtgg cggccttcta catcctgttc ttcaccgtta tcatctatgt tcggctggac    1380
ttctccatca ccaaggatcc agccgcagaa gccaggatga aggtagcctg catcacagag    1440
```

-continued

```
caggtcttga ccctggtcaa caagagaata ggcctttacc gtcactttga cgagaccgtc    1500
aataggtaca agcaatcccg ggacatctcc accctcaaca gtggcaagaa gagcctggag    1560
actgaacaca aggccttgac cagtgagatt gcactgctgc agtccaggct gaagacagag    1620
ggctctgatc tgtgcgacag agtgagcgaa atgcagaagc tggatgcaca ggtcaaggag    1680
ctggtgctga agtcggcggt ggaggctgag cgcctggtgg ctggcaagct caagaaagac    1740
acgtacattg agaatgagaa gctcatctca ggaaagcgcc aggagctggt caccaagatc    1800
gaccacatcc tggatgccct gtag                                           1824
```